United States Patent [19]
Opsal et al.

[11] Patent Number: 5,978,074
[45] Date of Patent: *Nov. 2, 1999

[54] APPARATUS FOR EVALUATING METALIZED LAYERS ON SEMICONDUCTORS

[75] Inventors: Jon Opsal, Livermore; Li Chen, Fremont, both of Calif.

[73] Assignee: Therma-Wave, Inc., Fremont, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/887,865

[22] Filed: Jul. 3, 1997

[51] Int. Cl.$^6$ .................................................. G01N 21/00
[52] U.S. Cl. ............................ 356/72; 356/376; 356/369; 356/364
[58] Field of Search ............................ 356/72, 376, 381, 356/382, 369, 364, 445

[56] References Cited

U.S. PATENT DOCUMENTS

| | | | |
|---|---|---|---|
| 4,468,136 | 8/1984 | Murphy et al. | 374/45 |
| 4,513,384 | 4/1985 | Rosencwaig | 364/563 |
| 4,521,118 | 6/1985 | Rosencwaig | 374/5 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,634,290 | 1/1987 | Rosencwaig et al. | 374/5 |
| 4,636,088 | 1/1987 | Rosencwaig et al. | 374/5 |
| 4,710,030 | 12/1987 | Tauc et al. | 356/432 |
| 4,795,260 | 1/1989 | Schuur et al. | 356/400 |
| 4,854,710 | 8/1989 | Opsal et al. | 356/432 |
| 4,999,014 | 3/1991 | Gold et al. | 356/382 |
| 5,042,951 | 8/1991 | Gold et al. | 356/369 |
| 5,074,669 | 12/1991 | Opsal | 356/445 |
| 5,159,412 | 10/1992 | Willenborg et al. | 356/445 |
| 5,181,080 | 1/1993 | Fanton et al. | 356/381 |
| 5,228,776 | 7/1993 | Smith et al. | 374/5 |
| 5,408,327 | 4/1995 | Geiler et al. | 356/432 |
| 5,657,754 | 8/1997 | Rosencwaig | 128/633 |

FOREIGN PATENT DOCUMENTS

| | | | |
|---|---|---|---|
| 0 432 963 A2 | 6/1991 | European Pat. Off. | G01N 21/17 |
| WO 83/03303 | 9/1983 | WIPO | G01N 21/63 |

OTHER PUBLICATIONS

J.T. Fanton & G.S. Kino, "High–sensitivity laser probe for photothermal measurements," *Appl. Phys. Lett.*, Jul. 13, 1987, vol. 51, No. 2, pp. 66–68.

J.T. Fanton, A. Kapitulnik, B.T. Khuri–Yakub & G.S. Kino, "Low–Temperature Photothermal Measurements of High $T_c$ Superconductors," *The Review of Progress in Quantitative Nondestructive Evaluation* (Reprint G.L. Report No. 4728 [Aug. 1990]), Presented Jul. 15–20, 1990, 8 pages in length.

B.C. Forget, I. Barbereau & D. Fournier, "Electronic diffusivity measurement in silicon by photothermal microscopy," *Appl. Phys. Lett.*, Aug. 19, 1996, vol. 69, No. 8, pp. 1107–1109.

(List continued on next page.)

*Primary Examiner*—Frank G. Font
*Assistant Examiner*—Reginald A. Ratiff
*Attorney, Agent, or Firm*—Limbach & Limbach L.L.P.

[57] ABSTRACT

An apparatus for characterizing multilayer samples is disclosed. An intensity modulated pump beam is focused onto the sample surface to periodically excite the sample. A probe beam is focused onto the sample surface within the periodically excited area. The power of the reflected probe beam is measured by a photodetector. The output of the photodetector is filtered and processed to derive the modulated optical reflectivity of the sample. Measurements are taken at a plurality of pump beam modulation frequencies. In addition, measurements are taken as the lateral separation between the pump and probe beam spots on the sample surface is varied. The measurements at multiple modulation frequencies and at different lateral beam spot spacings are used to help characterize complex multilayer samples. In the preferred embodiment, a spectrometer is also included to provide additional data for characterizing the sample.

56 Claims, 3 Drawing Sheets

OTHER PUBLICATIONS

J.T. Fanton, J. Opsal, D.L. Willenborg, S.M. Kelso & Al. Rosencwaig, "Multiparameter measurements of thin films using beam–profile reflectometry," *Journal of Applied Physics*, Jun. 1, 1993, vol. 73, No. 11, pp. 7035–7040.

A. Rosencwaig, "Depth Profiling of Integrated Circuits with Thermal Wave Electron Microscopy," *Electronic Letters*, Nov. 20th, 1980, vol. 16, No. 24, pp. 928–930.

J. Opsal & A. Rosencwaig, "Thermal and plasma wave depth profiling in silicon," *Appl. Phys. Lett.*, Sep. 1, 1985, vol. 47, No. 5, pp. 498–500.

A. Rosencwaig, Chapters 17, 18, and 21 *Photoacoustics and Photoacoustic Spectroscopy*, 1980, pp. 207–244 (Chapts. 17–18) and 270–284 (Chapt. 21).

X.D. Wu, G.S. Kino, J.T. Fanton & A. Kapitulnik, "Photothermal microscope for high–$T_c$ superconductors and charge density waves," *Rev. Sci. Instrum.*, Nov. 1993, vol. 64, No. 11, pp. 3321–3327.

A.M. Mansanares, T. Velinov, Z. Bozoki, D. Fournier & A.C. Boccara, "Photothermal microscopy: Thermal contrast at grain interface in sintered metallic materials," *J. Appl. Phys.*, vol. 75 (7), Apr. 1, 1994, pp. 3344–3350.

A.M. Mansanares, J.P. Roger, D. Fournier & A.C. Boccara, "Temperature field determination of InGaAsP/InP lasers by photothermal microscopy: Evidence for weak nonradiative processes at the facets," *Appl. Phys. Lett.*, vol. 64 (1), Jan. 3, 1994, pp. 4–6.

G. Langer, J. Hartmann & M. Reichling, "Thermal conductivity of thin metallic films measured by photothermal profile analysis," *Rev. Sci. Instrum.*, vol. 68 (3), Mar. 1997, pp. 1510–1513.

G. Savignat, P. Boch, L. Pottier, D. Vandembroucq & D. Fournier, "Non–destructive characterization of refractories by mirage effect and photothermal microscopy," *Journal De Physique IV*, Colloque C7, supplément au Journal de Physique III, vol. 3, Nov. 1993, pp. 1267–1272.

B.C. Forget, I. Barbereau, D. Fournier, S. Tuli & A.B. Battacharyya, "Electronic diffisivity measurement in silicon by photothermal microscopy," *Appl. Phys. Lett.*, vol. 69 (8), Aug. 19, 1996, pp. 1107–1109.

M.B. Suddendorf, M. Liu & M.G. Somekh, "Noncontacting measurement of opaque thin films using a dual beam thermal wave probe," *Appl. Phys. Lett.*, vol. 62 (25), Jun. 21, 1993, pp. 3256–3258.

M. Liu, M.B. Suddendorf & M.G. Somekh, "Response of interferometer based probe systems to photodisplacement in layered media," *J. Appl. Phys.*, vol. 76 (1), Jul. 1, 1994, pp. 207–215.

J.F. Bisson & D. Fournier, "Influence of diffraction on low thermal diffusivity measurements with infrared photothermal microscopy," *J. Appl. Phys.*, vol. 83 (2), Jan. 15, 1998, pp. 1036–1042.

E.P. Visser, E.H. Versteegen & W.J.P. van Enckevort, "Measurement of thermal diffusion in thin films using a modulated laser technique: Application to chemical–vapor–deposited diamond films," *J. Appl. Phys.*, vol. 71 (7), Apr. 1, 1992, pp. 3238–3248.

L. Pottier, "Micrometer scale visualization of thermal waves by photoreflectance microscopy," *Appl. Phys. Lett.*, vol. 64 (13), Mar. 28, 1994, pp. 1618–1619.

APPARATUS FOR EVALUATING METALIZED LAYERS ON SEMICONDUCTORS

TECHNICAL FIELD

The subject invention relates to a method and apparatus particularly suited for the nondestructive characterization of opaque layer structures on semiconductor samples.

BACKGROUND OF THE INVENTION

There is a great need in the semiconductor industry for metrology equipment which can provide high resolution, nondestructive evaluation of product wafers as they pass through various fabrication stages. In recent years, a number of products have been developed for the nondestructive evaluation of semiconductor samples. One such product has been successfully marketed by the assignee herein under the trademark Therma-Probe. This device incorporates technology described in the following U.S. Pat. Nos. 4,634,290; 4,636,088, 4,854,710 and 5,074,669. The latter patents are incorporated herein by reference.

In the basic device described in the patents, an intensity modulated pump laser beam is focused on the sample surface for periodically exciting the sample. In the case of a semiconductor, thermal and plasma waves are generated in the sample which spread out from the pump beam spot. These waves reflect and scatter off various features and interact with various regions within the sample in a way which alters the flow of heat and/or plasma from the pump beam spot.

The presence of the thermal and plasma waves has a direct effect on the reflectivity at the surface of the sample. Features and regions below the sample surface which alter the passage of the thermal and plasma waves will therefore alter the optical reflective patterns at the surface of the sample. By monitoring the changes in reflectivity of the sample at the surface, information about characteristics below the surface can be investigated.

In the basic device, a second laser is provided for generating a probe beam of radiation. This probe beam is focused colinearly with the pump beam and reflects off the sample. A photodetector is provided for monitoring the power of reflected probe beam. The photodetector generates an output signal which is proportional to the reflected power of the probe beam and is therefore indicative of the varying optical reflectivity of the sample surface.

The output signal from the photodetector is filtered to isolate the changes which are synchronous with the pump beam modulation frequency. In the preferred embodiment, a lock-in detector is used to monitor the magnitude and phase of the periodic reflectivity signal. This output signal is conventionally referred to as the modulated optical reflectivity (MOR) of the sample.

This system has the advantage that it is a non-contact, nondestructive technique which can be used on product wafers during processing. Using lasers for the pump and probe beams allows for very tight focusing, in the micron range, to permit measurements with high spatial resolution, a critical requirement for semiconductor inspection. The prior system has been used extensively in the past to monitor levels of ion doping in samples since the modulated optical reflectivity is dependent on ion dopant levels in the sample. This dependence is relatively linear for the low to mid-dose regimes ($10^{11}$ to $10^{14}$ ions/cm$^2$). At higher dopant concentrations, the MOR signal tends to become non-monotonic and further information is needed to fully analyze the sample.

One approach for dealing with the problem of monitoring samples with high dopant concentrations is to measure the DC reflectivity of both the pump and probe beams in addition to the modulated optical reflectivity signal carried on the probe beam. Using the DC reflectivity data at two wavelengths, some ambiguities in the measurement can often be resolved. The details of this approach are described in U.S. Pat. No. 5,074,669, cited above.

Semiconductor fabrication technology is increasing in complexity at a rapid pace. Various multilayer structures are being developed which makes testing more difficult. In addition, manufacturers are seeking to increase yields by fabricating chips on larger diameter wafers. As the diameter of the semiconductor wafers increases, the cost and value of each wafer increases. When using large, valuable and expensive wafers, it is no longer economically viable for manufacturers to rely on any forms of destructive testing methodologies. Therefore, there is a great need to provide equipment which can characterize complex structures with many unknowns or variables in a nondestructive manner.

Inspection problems also arise where metalized layers are deposited on semiconductors. If a typical metal layers is more than 100 angstroms thick, it will generally be opaque to more commonly used optical wavelengths. Therefore, equipment designed to monitor relatively transparent oxide layers cannot be effectively used to inspect metalized layers. Therefore, some new methodologies are required in order to inspect semiconductors with metalized layers. These layers can be formed from materials, such as aluminum, titanium, titanium nitride (TiN) and tungsten silicide (WSi).

SUMMARY OF THE INVENTION

In order to obtain sufficient information to characterize more complex samples, a system has been developed which substantially increases the amount of data that can be collected. The system of the subject invention includes an intensity modulated pump laser beam which is focused onto the sample in a manner to periodically excite the sample. A probe laser beam is focused onto the sample within the periodically heated area. A photodetector is provided for monitoring the reflected power of the probe beam and generating an output signal responsive thereto. The output signal is filtered and processed to provide a measure of the modulated optical reflectivity of the sample.

In accordance with the subject invention, the device further includes a steering means for adjusting the relative position of pump and probe beam spots on the sample surface. In the preferred embodiment, the steering means is used to move the beam spots from an overlapping, aligned position, to a separation of up to about 10 microns. Measurements can be taken as the separation of the beam spots is gradually changed or at discrete separation intervals.

This approach is particularly useful for monitoring the deposition of opaque, thin metal films. More specifically, the measurements taken at different spatial distances between the pump and probe beam spots can be used to help more accurately characterize the thermal diffusivity of the layer. This information can then be used by the processor to more accurately characterize the sample.

It should be noted that the concept of taking a measurement with a probe beam displaced from a pump beam can be found in the prior art. For example, in U.S. Pat. Nos. 4,521,118 and 4,522,510, both assigned to assignee herein and incorporated by reference, deformations at the sample surface, induced by periodic heating, are measured using a probe beam displaced from the pump beam. In the latter patents, periodic angular deviations of the probe beam are monitored. However, the latter patents do not teach or suggest that it would be desirable to take multiple measurements as the displacement between the two beams spots are varied.

Obtaining measurements from a probe beam displaced from a pump beam is also disclosed in U.S. Pat. No. 5,228,776, assigned to assignee herein and incorporated by reference. In this patent, an effort is made to align the pump and probe beams at the opposed ends of elongated conductive features within the sample. Further, the focal planes of the two beams are displaced vertically. In the principal embodiment of the U.S. Pat. No. 5,228,776 patent, the lateral spacing between the beams is selected and then fixed. There is no teaching in the U.S. Pat. No. 5,228,776 patent that it would be desirable to take multiple measurements as the displacement between the two beams is varied.

In the preferred embodiment of the subject invention, further information can be obtained by varying the modulation frequency of the pump beam. While it has been known that obtaining information as a function of modulation frequency is useful, the subject invention expands upon the past teachings by increasing the modulation range. In particular, in the prior art, the modulation range was typically in the 100 KHz to 1 MHz range. Some experiments utilized modulation frequency as high as 10 MHz. In the subject device, it has been found useful to take measurements with modulation frequencies up to 100 MHz range. At these high frequencies, the thermal wavelengths are very short, enabling information to be obtained for thin metal layers on a sample, on the order of 100 angstroms.

In the preferred embodiment of the subject invention, further information can be obtained by varying the spot sizes of either the pump or probe beams. Varying the spot size of the pump beam will vary the propagation characteristics of the thermal waves. Varying the spot size of the probe beam will vary the sensitivity of the system with respect to the depth of detection. By taking measurements at different spot sizes, some depth profiling information can be recorded and used to characterize the sample.

In the preferred embodiment of the subject invention, still further information can be derived by obtaining independent reflectivity measurements at a plurality of wavelengths. More specifically, the subject apparatus can further include a polychromatic light source generating a second probe beam which is directed to the sample surface. The reflected beam is captured by a detector which is capable of measuring power as a function of wavelength. These added measurements can also be used to help better resolve ambiguities in the analysis and improve the characterization of the sample.

It is also possible to add additional measurement modules which measure either reflectivity or ellipsometric parameters as a function of angle of incidence. Further, the system can also be used to monitor the periodic angular deviations of the probe beam to derive additional information.

Further objects of the subject invention will become apparent from the following detailed description, taken in conjunction with the drawings, in which:

DETAILED DESCRIPTION OF THE PREFERRED EMBODIMENT

Figure 1:
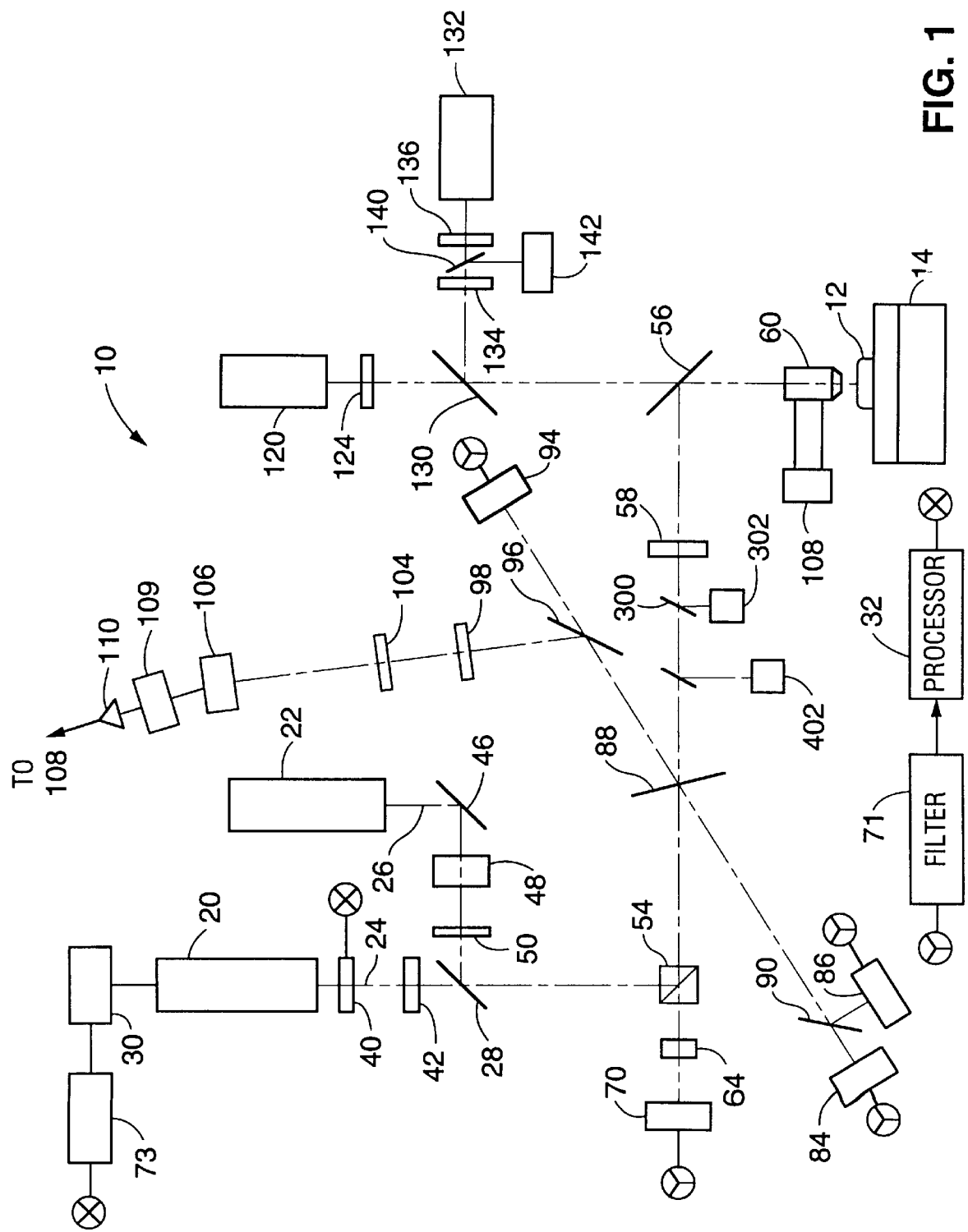
FIG. 1 is a schematic block diagram of the apparatus of the subject invention.

Turning to FIG. 1 there is shown a schematic diagram of the apparatus 10 of the subject invention. The apparatus 10 is intended to permit testing of a semiconductor sample 12 and in particular can be used to derive information about layers on the sample. Sample 12 is shown resting on a controllable stage 14. Stage 14 is capable of precise movements and functions to scan the sample with respect to the laser beams.

In the preferred embodiment, the apparatus 10 includes a pump laser 20 for exciting the sample and a probe laser 22 for monitoring the sample. Gas, solid state or semiconductor lasers can be used. As described in the assignees earlier patents, other means for exciting the sample can include different sources of electromagnetic radiation or particle beams such as from an electron gun.

In the preferred embodiment, semiconductor lasers are selected for both the pump and probe lasers due to their reliability and long life. In the illustrated embodiment, pump laser 20 generates a near infrared output beam 24 at 790 nm while probe laser 22 generates a visible output beam 26 at 670 nm. Suitable semiconductor lasers for this application include the Mitsubishi ML6414R (operated at 30 mW output) for the pump laser and a Toshiba Model 9211 (5 mW output) for the probe laser. The outputs of the two lasers are linearly polarized. The beams are combined with a dichroic mirror 28. It is also possible to use two lasers with similar wavelengths and rely on polarization discrimination for beam combining and splitting.

Pump laser 20 is connected to a power supply 30 which is under the control of a processor 32. The output beam of laser 20 is intensity modulated through the output of power supply 30. The modulation frequency has a range running from 100 KHz to 100 MHz. In the preferred embodiment, the modulation frequency can be set up to 125 MHz. As described in the above cited patents, if an ion laser is used to generate the pump beam, the intensity modulation can be achieved by a separate acousto-optic modulator.

Prior to reaching the beam combining mirror 26, the probe beam 24 passes through a tracker 40 and a shutter 42. Tracker 40 is used to control the lateral position of beam 24 with respect to the probe beam as discussed more fully hereinbelow. The shutter 42 is used to block the pump beam when other measurements which do not require periodic excitation are being taken.

The beam 26 from probe laser 22 is turned by mirror 46 and passed through a collimator 48 which is used to match the focal plane of the probe laser spot with the pump laser spot. A shutter 50 is also located in the path of the probe beam 26 to block the probe beam when measurements that do not use the probe are being taken, so that no stray probe beam light hits the detector.

After the beams 24 and 26 are combined, they are redirected through polarizing beam splitter 54 to another beam splitter 56. In between, the beams pass through a quarter-wave plate 58 for rotating the polarization of the beams by 45 degrees. The beams are directed down to the sample 12 through a microscope objective 60. Objective 60 has a high n.a., on the order of 0.9, and is capable of focusing the beam to a spot size on the order of a few microns and preferably close to one micron in diameter. The spacing between the objective and the sample is controlled by an autofocus system described in greater detail hereinbelow.

The returning reflected beams 24 and 26 pass through the quarter-wave plate 58 a second time, resulting in another 45 degree polarization rotation. This second rotation allows the beams to pass through the beam splitter 54. A filter 64 is provided to remove the pump beam light 24 allowing the probe beam light to fall on the photodetector 70. Detector 70 provides an output signal which is proportional to the power of the reflected probe beam 26. Detector 70 is arranged to be underfilled so that its output can be insensitive to any changes in beam diameter or position. In the preferred embodiment, detector 70 is a quad cell generating four separate outputs. When used to measure reflected beam power, the output of all four quadrants are summed. When the subject apparatus is operated to measure beam deflection, the output of one adjacent pair of quadrants is summed and subtracted from the sum of the remaining pair of quadrants. This later measurement will be discussed below.

The output of the photodetector 70 is passed through a low pass filter 71 before reaching processor 32. One function of filter 71 is to pass a signal to the processor 32 proportional to the DC power of the reflected probe. A portion of filter 71 also functions to isolate the changes in power of the reflected probe beam which are synchronous with the pump beam modulation frequency. In the preferred embodiment, the filter 71 includes a lock-in detector 72 for monitoring the magnitude and phase of the periodic reflectivity signal. Because the modulation frequency of pump laser can be so high, it is preferable to provide an initial down-mixing stage for reducing the frequency of detection.

Figure 2:
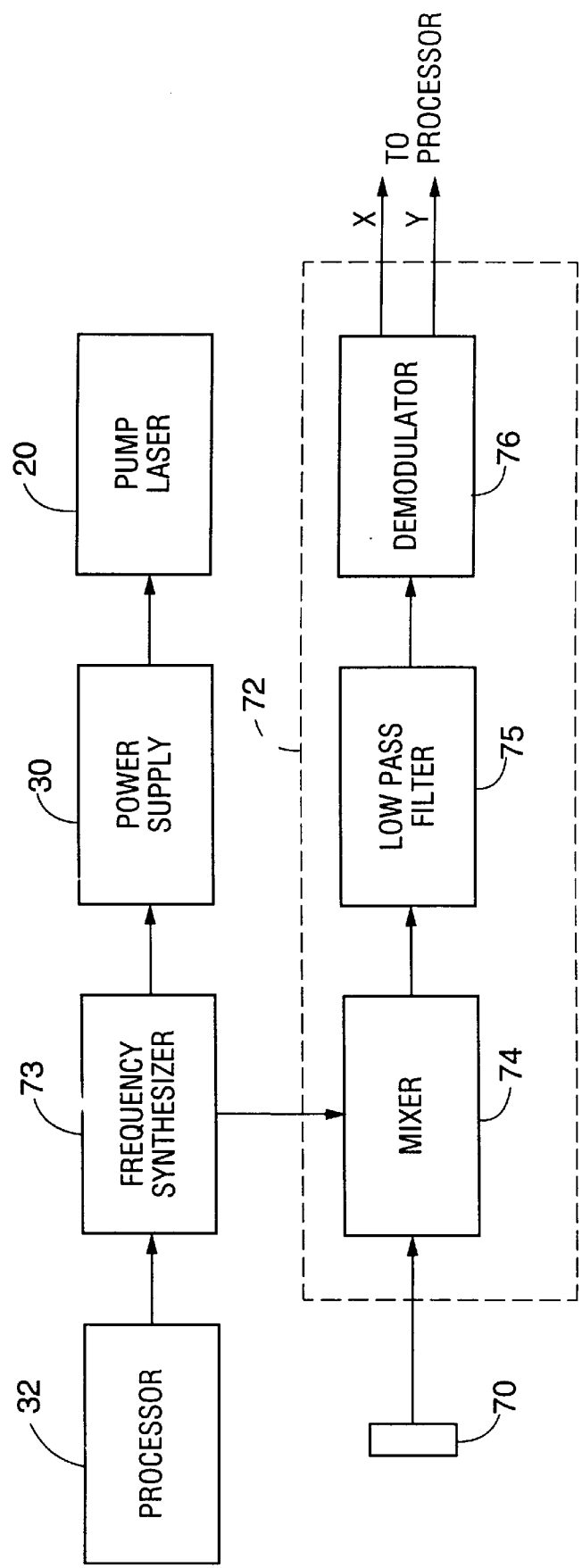
FIG. 2 is a schematic diagram of a frequency synthesizer and lock-in amplifier for electronically down mixing the high frequency MOR signal to create a low frequency heterodyne signal output.

A schematic diagram of the frequency generation and detection stage is illustrated in FIG. 2. As shown therein, a frequency synthesizer 73 is provided for generating the various pump beam modulation frequencies. Synthesizer 73 is under the control of processor 32 and can generate an output from 100 KHz to at least 125 KHz. This output is delivered as a signal to the power supply 30 of laser 20.

Synthesizer 73 also generates an electronic heterodyne signal for delivery to the lock-in amplifier 72. The heterodyne signal will be close to, but different from the signal sent to the pump laser. For example, the heterodyne signal can be 10 KHz higher than the signal sent to the pump laser.

The heterodyne signal from the synthesizer is combined with the output from the signal detector 70 in a mixer 74. The output of the mixer will include signal components at both the sum and difference of the two input signals. The difference signal will be at the relatively low frequency of 10 KHz. All the signals are passed through a low pass filter 75 to eliminate the high frequency components from the synthesizer and the detector. The low frequency signal is then demodulated by demodulator 76. The outputs of demodulator 76 are the "in-phase" and "quadrature" signals typical of a lock-in amplifier. The in-phase and quadrature signals can be used by processor 32 to calculate the magnitude and the phase of the modulated optical reflectivity signal.

In initial experiments, a model SR844 lock-in detector from Stanford Research Systems was utilized. This device utilizes a combination of analog and digital techniques to permit operation over a wide frequency range. In this device, an internal frequency synthesizer is used to modify the incoming reference signal from the synthesizer to generate two reference signals which differ in phase by 90 degrees. These reference signals are mixed with the incoming signals from the detector 70. After filtering, the low frequency signals are digitized by two 16-bit analog-to-digital converters. The digital low frequency signals are supplied to a DSP chip for analysis.

As an alternative to using an electronic heterodyne downmixing system, it is also possible to reduce the frequency of detection using an optical heterodyne approach. Such an optical approach is disclosed in U.S. Pat. No. 5,408,327, incorporated herein by reference. In the latter system, both of the laser beams are modulated but at slightly different frequencies. Both beams generate thermal and plasma waves at their respective modulation frequencies. The beam from one laser picks up an intensity modulation upon reflection due to the modulated optical reflectivity induced in the sample by the other beam. The MOR signal picked up upon reflection "mixes" with the inherent modulation of the beam, creating additional modulations in the beam at both the sum and difference frequency. This process is analogous to electrical heterodyning. The difference or "beat" frequency is much lower than either of the initial beam modulation frequencies and can therefore be detected by a low frequency lock-in amplifier.

It should be noted that in the latter arrangement, both beams carry the desired MOR signal and either one or both of the reflected beams can be measured. Therefore, in the latter system, the term probe beam could be applied to either laser beam. It should also be noted that when some samples are exited with two modulation frequencies, nonlinear effects in the sample may result in periodic excitation at the sum and difference frequencies in the sample. This effect is usually relatively small.

To insure proper repeatability of the measurements, the signals must be normalized in the processor. As noted above, the DC reflectivity of the probe beam is derived from detector 70. In addition, the DC output powers of the pump and probe lasers are monitored by incident power detectors 84 and 86 respectively. A wedge 88 functions to pick off about one percent of the incident beam power and redirects it to an edge filter 90 for separating the two beams. The outputs of the detector 84 and 86 are passed through the low pass portion of filter 71 and into the processor 32.

The signals are further normalized by taking a measurement of the power of the pump beam 24 after it has been reflected. This measurement is used to determine the amount of pump energy which has been absorbed in the sample. The pump beam reflected power is measured by detector 94. Wedge 88 functions to pick off about one percent of the returning beams which are redirected to edge filter 96. The DC signal for both the incident pump and probe beam powers as well as the reflected beam powers are used to correct for laser intensity fluctuations and absorption and reflection variations in the samples. In addition, the signals can be used to help calculate sample parameters.

An autofocus mechanism is used to maintain the spacing between the objective 60 and the sample 12 to be equal to the focal length of the objective. This distance can be maintained to less than one hundredth of a micron.

The autofocus mechanism includes a servo motor 108 for varying the vertical position of the objective 60. The servo is driven by an analog detection loop which determines if the objective 60 is properly focusing the probe beam. As seen in FIG. 1, a small portion of the reflected probe beam light picked off by the wedge 88 is redirected by filter 96 into the main elements of the autofocus detection loop. The probe beam is focused by a lens 98 through a chopper wheel 104 located in the focal plane of the lens 98. The light passing the chopper wheel 104 is imaged on a split-cell photodetector 106.

If the objective 60 is out of focus, there will be a phase difference in the light striking the two sides of the split cell detector 106 which is measured by a phase detector 109. The phase difference is used as an input to an amplifier 110 which in turn drives the servo 108. This approach to autofocusing is known as the automated Foucault knife edge focus test. This system can also be used to intentionally defocus the beams, thereby varying the spot sizes of the pump and probe beams. This adjustment can be used to gain further information as discussed below.

In the preferred embodiment, a polychromatic, or white light source 120 is provided to illuminate the sample to permit viewing on a TV monitor (not shown). The beam 122 from the white light source 120 is passed through a shutter 124. When measurements with the lasers 20 and 22 are being taken, the shutter is closed so no stray white light gets into the detection system.

A portion of the white light returning from the sample is redirected by a beam splitter 130 to a CCD camera 132 for generating an image for the TV monitor. The beam will pass through a CCD lens 134 and a filter 136. Filter 136 functions to reduce the amount of laser light reaching the camera. In the preferred embodiment, a portion of the light is redirected by a beam splitter 140 into an array spectrograph 142 more fully described herein below.

Having described the basic elements of the subject invention, its operation will now be discussed.

In use, a sample 12 is placed on the stage 14. Measurements at various points on the sample can be made by rastering the stage to the desired location. During initial set up of a fabrication procedure, a relatively high number of test points may be desired. Once the fabrication procedure is up and running, only spot checks of the wafer are typically made. This will often entail measuring from five to twenty-five spots on a wafer.

At each measurement point, the pump and probe laser beams 24 and 26 are activated. In a typical measurement, the beams will be initially colinearly aligned. Exact overlap will typically provide the strongest modulated optical reflectivity signal. Measurements can then be taken at a plurality of modulation frequencies of the pump beam. The range of modulation frequencies and the number of frequencies is selected by the operator. As noted above, in the preferred embodiment, the range of pump beam modulation frequencies covers from 100 KHz to 125 MHz. The output from the photodetector 70 is passed through the filter 71 (including lock-in 72) to the processor which records the magnitude and/or phase of the modulated optical reflectivity signal for each of the modulation frequencies selected.

In accordance with the subject invention, once the desired measurements are completed with the beam spots in an overlapping, aligned position, the processor signals the tracker 40 to adjust the position of the pump beam 24 so that pump and probe beam spots on the sample surface are laterally displaced. In one possible scenario, the beams are initially displaced a distance of one micron. Once in this position, a series of measurements are taken at different modulation frequencies in the manner described above. Once again, the processor will record the modulated optical reflectivity signal at each of these modulation frequencies.

In accordance with the subject invention, once the second set of measurements are complete, the processor will again command the tracker 40 to further separate the pump and probe beam spots to a distance of two microns. Measurements will then be taken at this two micron spacing and at subsequent spacings, each time increasing the spacing by one micron. It is envisioned that for complex samples, measurement might be taken at successive increments of 0.5 microns. Alternatively, measurements can be taken as the separation of the two beam spots is continuously increased. The span of spacings between beam spots can range from overlapping to about 10 microns.

It is envisioned that the user will be able to determine what sort of scanning algorithm is best suited to the particular test situation. Variables such as separation distance and number of measurements at each separation can be entered by the user through a software interface.

Once all of the measurements at various spacings and modulation frequencies have been taken and stored, the processor will attempt to characterize the sample. Various types of modeling algorithms can be used depending on the complexity of the sample. Optimization routines which use iterative processes such as least square fitting routines are typically employed. One example of this type of optimization routine used for thermal wave analysis is described in "Thermal Wave Measurements and Monitoring of $TASi_x$ Film Properties," Smith, et. al., Journal of Vacuum Science and Technology B, Vol. 2, No. 4, p. 710, 1984. An optimization routine used for more general optical analysis can be found in "Multiparameter Measurements of Thin Films Using Beam-Profile Reflectivity," Fanton, et. al., Journal of Applied Physics, Vol. 73, No. 11, p.7035, 1993.

It has been found that measurements taken at different beam spot spacings are particularly useful in characterizing thermal diffusivity of a sample. Identification of this parameter can be used to determine the structure of the sample. In addition, measurements at very high modulation frequencies are useful for very thin films, since the wavelength of the thermal and plasma waves is very short.

In the preferred embodiment of the subject invention, further information can be obtained by varying the spot sizes of either of both of the pump and probe beams. Varying the spot sizes of the beams will vary the propagation and detection characteristics of the thermal waves. In particular, when using a highly focused pump beam spot size, the thermal waves will tend to propagate in all directions (3 dimensionally) away from the area of focus. In contrast, as the pump beam spot size increases, the thermal waves will tend to propagate in a more 1-dimensional manner, perpendicular to the area of focus.

With respect to the detection, a very large probe beam spot tends to see mostly the 1-dimensional component of the thermal wave. In contrast, a highly focused probe beam, being more localized, is sensitive to the 3-dimensional character of the thermal waves. This variation in the generation and detection characteristics of thermal waves is characterized by the square root of the sum of the squares of the pump and probe beam diameters. When this value is small compared to the thermal diffusion length, the measurement is 3-dimensional in character and when the value is large compared to the thermal diffusion length, the measurement is 1-dimensional in character. By taking measurements at different pump and/or probe beam spot sizes, some depth profiling information can be recorded and used to characterize the sample.

As noted above, the spot size of both the beams can be controlled by the autofocus system. In order to increase the size of the beam spots, the processor can add an offset to the focusing algorithm which would defocus the beams. The beam spots can be made of different sizes by adjusting the collimator 48. In the preferred embodiment, measurements are taken and recorded at various beam spot sizes ranging from one micron to ten microns. This additional information can be used to characterize the sample.

In the preferred embodiment of the subject invention, still further measurements can be taken to reduce the ambiguities of analysis. More specifically, in addition to the modulated optical reflectivity measurements, it is also desirable to monitor the periodic angular deflections of the probe beam due to deformations in the surface of the sample induced by the periodic heating. This type of measurement is described in detail in U.S. Pat. Nos. 4,521,118 and 4,522,510, cited above. As described in those patents, because of the thermal expansion properties of samples, the periodic heating by the pump beam will create a time varying "bump" in the sample surface. If the pump and probe beam are spaced apart, the probe beam will undergo periodic angular deviations at the frequency of the modulated heating. These angular deviations can be measured by a split cell detector. The output of the split cell is sent to the filter and the processor. The processor functions to calculate the magnitude and phase of the deflection signal that is synchronous with the pump beam modulation frequency.

Figure 3:
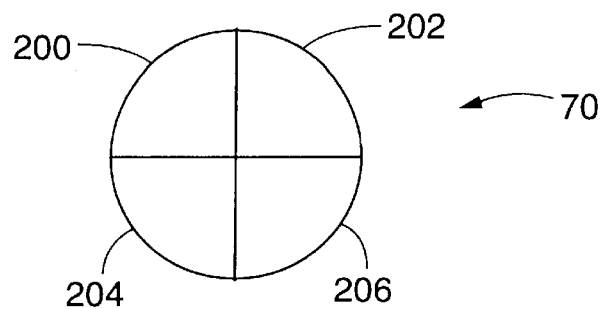
FIG. 3 is a schematic diagram of a quad cell photodetector.

As noted earlier, detector 70 is preferably a quad cell detector, or a detector with four quadrants each generating separate output signals. Deflections of the probe beam in both the X and Y axis due to angular deviations of the probe beam can be measured with such a detector. More specifically and as shown in FIG. 3, to determine the deflection of the probe beam in the X axis, the outputs of quadrants 200 and 202 are summed and subtracted from the sum of quadrants 204 and 206. Alternatively, to determine the deflection of the probe beam in the Y axis, the outputs of quadrants 200 and 204 are summed and subtracted from the sum of quadrants 202 and 206. It should be noted that these type of measurements function to cancel out any changes in the reflected power of the beam. As noted above, in operation, the output of all four detector quadrants are fed to the filter 71 and processor 32. If the output of the four quadrants is summed, the MOR signal is obtained. If the quadrant halves are summed and subtracted, the probe beam deflection signal can be obtained.

In use, the deflection signal can be recorded for each of the beam spot positions and modulation frequencies. In practice, there will usually be little or no deflection signal when the two beam spots are colinearly aligned. However, as soon as the centers of the beam spots are separated, a signal can be often be detected, even if the beams are in a partially overlapping configuration.

In the preferred embodiment, the subject apparatus further includes a spectrometer for providing additional data. As noted above, a white light source 120 is necessary for illuminating the sample for tracking on a TV monitor. This same light source can be used to provide spectral reflectivity data.

Figure 4:
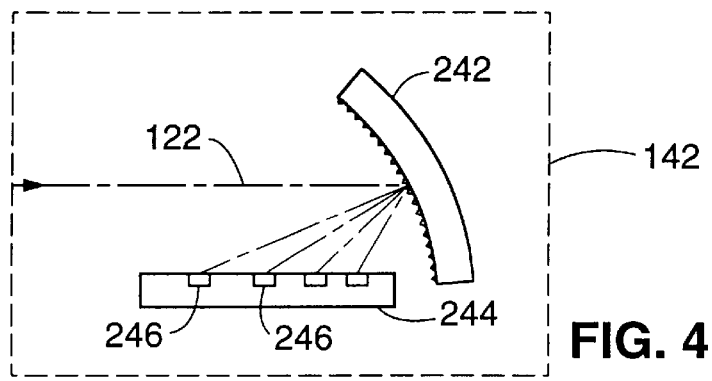
FIG. 4 is a schematic diagram of an array spectrometer.

As seen in FIG. 1, a beam splitter can be used to redirect a portion of the reflected white light to a spectrometer 142. The spectrometer can be of any type commonly known and used in the prior art. FIG. 4 illustrates one form of a spectrometer. As seen therein, the white light beam 122 strikes a curved grating 242 which functions to angularly spread the beam as a function of wavelength. A photodetector 244 is provided for measuring the beam. Detector 244 is typically a photodiode array with different wavelengths or colors falling on each element 246 in the array. The outputs of the diode array are sent to the processor for determining the reflectivity of the sample as a function of wavelength. This information can be used by the processor during the modeling steps to help further characterize the sample.

Figure 5:
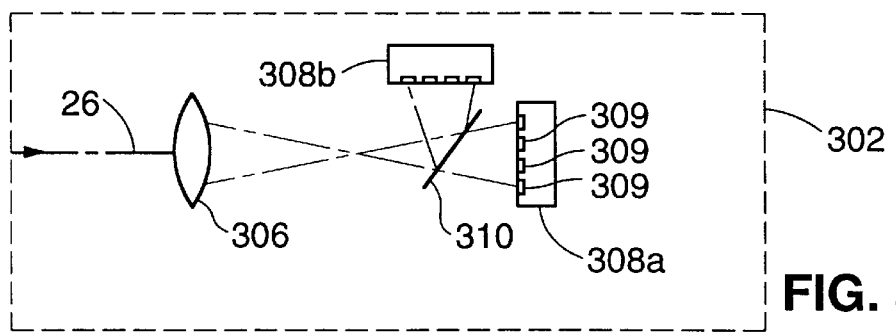
FIG. 5 is a schematic diagram of the detection module for simultaneously determining the reflectivity of rays within a beam striking the sample at multiple angles of incidence.

It is also possible to provide a mechanism for measuring sample reflectivity as a function of the angle of incidence of the beam. To achieved this goal, a portion of the reflected probe beam light 26 can be picked off by wedge 300. This light is sent to a beam profile reflectometer module 302 as more clearly shown in FIG. 5. When taking these measurements, the pump beam is preferably turned off so that the probe beam will not be modulated.

Module 302 is of the type described in U.S. Pat. No. 4,999,014 assigned to the assignee herein and incorporated by reference. As described therein, if a probe beam is focused onto a sample with a strong lens, various rays within the beam will strike the sample surface at a range of angles of incidence. If the beam is properly imaged with a relay lens 306, the various rays can be mapped onto a linear photodiode array 308. The higher angles of incidence rays will fall closer to the opposed ends of the array. The output from each element 309 in the diode array will correspond to different angles of incidence. Preferably, two orthogonally disposed arrays 308a and 308b are provided to generate angle of incidence information in two axes. A beam splitter 310 is used to separate the probe beam into two parts so both axes can be detected simultaneously. The output of the arrays will supplied to the processor 32 for storage. The data can be used to further characterize the sample.

Figure 6:
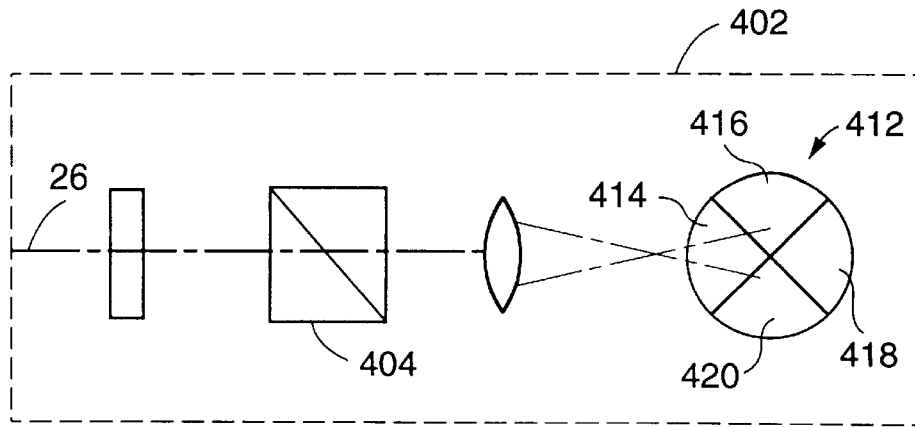
FIG. 6 is a schematic diagram of a detection module for determining ellipsometric parameters of a sample by analyzing a reflected probe beam and which includes integrated data over multiple angles of incidence with respect to the sample surface.

In still a further preferred embodiment, ellipsometric information can be derived from the sample using the reflected probe beam. As in the previous example, the pump beam should be turned off for these measurements. As seen in FIG. 1, a portion of the reflected probe beam can be picked off by a beam splitter 400 and redirected to a beam profile ellipsometer 402 as shown in FIG. 6. A suitable beam profile ellipsometer is described in U.S. Pat. No. 5,181,080, assigned to the assignee herein and incorporated by reference.

As described above, the rays in the reflected probe beam correspond to different angles of incidence. By monitoring the change in polarization state of the beams (from the original linear polarization, to elliptical polarization upon reflection), ellipsometric information, such as $\psi$ and $\Delta$, can be determined.

To determine this information, the beam is first passed through a quarter-wave plate 404 for retarding the phase of one of the polarization states of the beam by 90 degrees. The beam is then passed through a polarizer 408 which functions to cause the two polarization states of the probe beam to interfere with each other. The light is then passed through an imaging lens 410 an onto a quadrant detector 412. Each quadrant, 414, 416, 418, and 420 generate separate output signals proportional to the power of the probe beam striking that quadrant. These signals represents an integration of the intensities of all the rays having different angles of incidence with respect to the sample surface. As described in U.S. Pat. No. 5,181,080, ellipsometric information can be obtained if the signals from opposing quadrants 414 and 418 are summed and subtracted from the sum of the signals from opposing quadrants 412 and 420. The output of detector 412 is sent to the processor 32 for storage and use in characterizing the sample.

As can be seen, the subject device can be used to provide a large amount of measurement data in order to better resolve the characteristics of the sample. Such complete measurements are often necessary in order to determine the composition of a multilayer structure.

While the subject invention has been described with reference to a preferred embodiment, various changes and modifications could be made therein, by one skilled in the art, without varying from the scope and spirit of the subject invention as defined by the appended claims.

We claim:

1. An apparatus for evaluating the characteristics of a sample comprising:

an intensity modulated pump laser beam, said pump beam being directed to a spot on the surface of the sample for periodically exciting the sample;

a probe laser beam being directed to a spot on the surface of the sample within a region that has been periodically excited and is reflected therefrom;

a photodetector for measuring the power of the reflected probe beam and generating an output signal in response thereto;

means for adjusting the spot size of either or both of the pump or probe beams on the surface of the sample; and processor for filtering the output signal to provide a measure of the magnitude or phase of the modulated optical reflectivity of the sample, said processor further functioning to control the spot size adjustment means in a manner so that a plurality of measurements are taken and recorded at a plurality of different spot sizes with the plurality of measurements being used to evaluate the characteristics of the sample.

2. An apparatus as recited in claim 1 wherein the size of the beam spots is varied from a few microns in diameter to ten microns in diameter.

3. An apparatus as recited in claim 1 further including a steering means for adjusting the lateral separation between the pump and probe laser beam spots on the surface of the sample and wherein a plurality of measurements are taken at different separations between the pump and probe laser beam spots and wherein the processor uses the measurements at spot separations to evaluate the characteristics of the sample.

4. An apparatus as recited in claim 1 further including a means for varying the modulation frequency of the pump laser beam and wherein a plurality of measurements are taken at different modulation frequencies and with different beam spot separations to facilitate the evaluation of the sample.

5. An apparatus as recited in claim 2 wherein the modulation frequency of the pump laser beam can be varied from 100 KHz to 100 MHz.

6. An apparatus as recited in claim 3 wherein the photodetector measures the periodic angular deflections of the probe laser beam and wherein the processor uses the angular deflection measurements to evaluate the characteristics of the sample.

7. An apparatus as recited in claim 3 further including a detector means for measuring the intensity of rays within the probe beam as a function of the angle of incidence with respect to the sample surface and wherein the processor uses the angle of incidence measurements to evaluate the characteristics of the sample.

8. An apparatus as recited in claim 3 further including a detector means for measuring the change in polarization state of the reflected probe beam and wherein the processor uses the polarization state measurements to evaluate the characteristics of the sample.

9. An apparatus as recited in claim 8 wherein the detector means generates an output signal that represents an integration of rays within the probe beam having multiple angles of incidence with respect to the sample surface.

10. An apparatus as recited in claim 3 further including a broadband polychromatic light source for generating a polychromatic probe beam, said polychromatic probe beam being directed to a spot on the surface of the sample and is reflected therefrom, said apparatus further including a detector means for measuring the power of the reflected polychromatic light beam and generating a plurality of second output signals corresponding to a plurality of different wavelengths within the polychromatic beam and wherein the processor uses the second output signals to evaluate the characteristics of the sample.

11. An apparatus for evaluating the characteristics of a sample, comprising:

an intensity modulated pump laser beam, said pump beam being directed to a spot on the surface of the sample for periodically exciting the sample;

a probe laser beam being directed to a spot on the surface of the sample within a region which has been periodically excited and is reflected therefrom;

a photodetector for measuring the power of the reflected probe laser beam and generating a first output signal in response thereto;

a broadband polychromatic light source for generating a polychromatic probe beam, said polychromatic probe beam being directed to a spot on the surface of the sample and is reflected therefrom;

detector means for measuring the power of the reflected polychromatic probe beam and generating a plurality of second output signals corresponding to a plurality of different wavelengths within the polychromatic probe beam; and processor for filtering the first output signal to provide a measure of the magnitude or phase of the modulated optical reflectivity of the sample, said processor further functioning to monitor the second output signals with the first and second output signals being used to evaluate the characteristics of the sample.

12. An apparatus as recited in claim 11 wherein the probe beam from the polychromatic light source is directed to the same location as the probe laser beam is directed.

13. An apparatus as recited in claim 11 further including a steering means for adjusting the lateral separation between the pump and probe laser beam spots on the surface of the sample and wherein a plurality of measurements are taken at different separations between the pump and probe laser beam spots.

14. An apparatus as recited in claim 11 wherein said steering means functions to separate the pump and probe laser spots beams over a range from an aligned overlapping position to a spacing of at least 10 microns.

15. An apparatus as recited in claim 11 further including a means for varying the modulation frequency of the pump laser beam and wherein a plurality of measurements are taken at different modulation frequencies and with different beam spot separations to facilitate the evaluation of the sample.

16. An apparatus as recited in claim 15 wherein the modulation frequency of the pump laser beam can be varied from 100 KHz to 100 MHz.

17. An apparatus as recited in claim 13 further including a means for varying the size of either or both of the pump and probe laser beam spots and wherein the reflected power of the probe laser beam is measured as the size of the spots is varied and wherein the processor uses the measurements at different spot sizes to evaluate the characteristics of the sample.

18. An apparatus as recited in claim 13 wherein the photodetector measures the periodic angular deflections of the probe laser beam and wherein the processor uses the angular deflection measurements to evaluate the characteristics of the sample.

19. An apparatus as recited in claim 13 further including a second detector means for measuring the intensity of rays within the probe laser beam as a function of the angle of incidence with respect to the sample surface and wherein the processor uses the angle of incidence measurements to evaluate the characteristics of the sample.

20. An apparatus as recited in claim 13 further including a second detector means for measuring the change in polarization state of the reflected probe beam and wherein the processor uses the polarization state measurements to evaluate the characteristics of the sample.

21. An apparatus as recited in claim 20 wherein the second detector means generates an output signal that represents an integration of rays within the probe beam having multiple angles of incidence with respect to the sample surface.

22. A method for determining the thickness of a thin metal layer formed on a semiconductor substrate comprising the steps of:
   directing an intensity modulated pump laser beam to a spot on the surface of the sample for periodically exciting the sample;
   directing a probe laser beam to a spot on the surface of the sample within a region that has been periodically excited and is reflected therefrom;
   varying the modulation frequency of the pump laser beam wherein the lowest modulation frequency is at least 100 Khz;
   varying the separation between the pump and probe beam spots;
   measuring the power of the reflected probe beam and generating an output signal in response thereto at various modulation frequency and beam spot separations; and
   filtering the output signals to provide a measure of the magnitude or phase of the modulated optical reflectivity of the sample, at various modulation frequencies and beam spot separations and using said measurements to calculate the thickness of the metal layer on the substrate.

23. A method for determining the thickness of a thin metal layer formed on a semiconductor substrate comprising the steps of:
   directing an intensity modulated pump laser beam to a spot on the surface of the sample for periodically exciting the sample wherein the modulation frequency of the pump beam is at least 100 Khz;
   directing a probe laser beam to a spot on the surface of the sample within a region that has been periodically excited and is reflected therefrom;
   varying the separation between the pump and probe beam spots;
   measuring the power of the reflected probe beam and generating an output signal in response thereto at various beam spot separations; and
   filtering the output signals to provide a measure of the magnitude or phase of the modulated optical reflectivity of the sample, at various beam spot separations and using said measurements to calculate the thickness of the metal layer on the substrate.

24. A method for evaluating the characteristics of a sample comprising the steps of:
   directing an intensity modulated pump laser beam to a spot on the surface of the sample for periodically exciting the sample;
   directing a probe laser beam to a spot on the surface of the sample within a region that has been periodically excited and is reflected therefrom;
   varying the size of either or both of the pump and probe beam spots on the sample;
   measuring the power of the reflected probe beam and generating an output signal in response thereto at various beam spot sizes; and
   filtering the output signals to provide a measure of the magnitude or phase of the modulated optical reflectivity of the sample at various beam spot sizes and using said measurements to evaluate the characteristics of the sample.

25. A method as recited in claim 24 wherein the size of the spot on the sample is varied between a few microns in diameter to ten microns in diameter.

26. A method for evaluating the characteristics of a sample comprising the steps of:
   directing an intensity modulated pump laser beam to a spot on the surface of the sample for periodically exciting the sample;
   directing a probe laser beam to a spot on the surface of the sample within a region that has been periodically excited and is reflected therefrom;
   measuring the power of the reflected probe beam and generating an output signal in response thereto;
   filtering the output signals to provide a measure of the magnitude or phase of the modulated optical reflectivity of the sample;
   directing a broadband, polychromatic light beam onto a spot on the surface of the sample;
   measuring the intensity of the reflected polychromatic light beam and generating a plurality of second output signals corresponding to a plurality of different wavelengths within the polychromatic beam; and
   evaluating the characteristics of the sample using the modulated optical reflectivity measurements and the measurements at different wavelengths.

27. A method as recited in claim 26 further including the step of varying the modulation frequency of the pump laser and measuring the power of the reflected probe beam at a plurality of modulation frequencies and using the measurements to characterize the sample.

28. A method as recited in claim 27 further including the step of varying the separation between pump and probe laser beam spots on the sample surface and measuring the power of the reflected probe beam at a plurality of separations and using the measurements to characterize the sample.

29. A method as recited in claim 28 further including the step of varying the size of either of both of the pump and probe laser beam spots on the sample surface and measuring the power of the reflected probe beam at a plurality of pump and probe beam spot sizes and using the measurements to characterize the sample.

30. A method as recited in claim 27 wherein measurements are taken as the separation between the pump and probe laser beam spots is continuously changed.

31. A method as recited in claim 27 wherein measurements are taken at discrete separation intervals between the pump and probe laser beam spots.

32. A method as recited in claim 27 wherein the spacing between the pump and probe beam spots is varied over a range from an aligned overlapping position to a spacing of at least 10 microns.

33. A method as recited in claim 27 wherein the modulation frequency of the pump laser beam can be varied from 100 KHz to 100 MHz.

34. A method as recited in claim 27 further including the step of measuring the periodic angular deflections of the probe laser beam and using those measurements to evaluate the characteristics of the sample.

35. A method as recited in claim 27 further including the step of measuring the intensity of rays within the probe laser beam as a function of the angle of incidence with respect to the sample surface and using the angle of incidence measurements to evaluate the characteristics of the sample.

36. A method as recited in claim 27 further including the step of measuring the change in polarization state of the reflected probe beam and using the measurements to evaluate the characteristics of the sample.

37. A method as recited in claim 36 wherein the step of measuring the change of polarization state of the reflected probe beam includes generating an output signal that represents an integration of rays within the probe beam having multiple angles of incidence with respect to the sample surface.

38. A method as recited in claim 22 wherein measurements are taken as the separation between the pump and probe laser beam spots is continuously changed.

39. A method as recited in claim 22 wherein measurements are taken at discrete separation intervals between the pump and probe laser beam spots.

40. A method as recited in claim 22 wherein the spacing between the pump and probe beam spots is varied over a range from an aligned overlapping position to a spacing of at least 10 microns.

41. A method as recited in claim 22 wherein the modulation frequency of the pump laser beam is varied from 100 KHz to 100 MHz.

42. A method as recited in claim 22 further including the step of varying the size of either of both of the pump and probe laser beam spots on the sample surface and measuring the power of the reflected probe beam at a plurality of pump and probe beam spot sizes and using the measurements to characterize the sample.

43. A method as recited in claim 22 further including the step of measuring the periodic angular deflections of the probe laser beam and using those measurements to evaluate the characteristics of the sample.

44. A method as recited in claim 22 further including the step of measuring the intensity of rays within the probe laser beam as a function of the angle of incidence with respect to the sample surface and using the angle of incidence measurements to evaluate the characteristics of the sample.

45. A method as recited in claim 22 further including the step of measuring the change in polarization state of the reflected probe beam and using the measurements to evaluate the characteristics of the sample.

46. A method as recited in claim 45 wherein the step of measuring the change of polarization state of the reflected probe beam includes generating an output signal that represents an integration of rays within the probe beam having multiple angles of incidence with respect to the sample surface.

47. A method as recited in claim 23 wherein measurements are taken as the separation between the pump and probe laser beam spots is continuously changed.

48. A method as recited in claim 23 wherein measurements are taken at discrete separation intervals between the pump and probe laser beam spots.

49. A method as recited in claim 23 wherein the spacing between the pump and probe beam spots is varied over a range from an aligned overlapping position to a spacing of at least 10 microns.

50. A method as recited in claim 23 further including the step of varying the modulation frequency of the pump laser and measuring the power of the reflected probe beam at a plurality of modulation frequencies and using the measurements to characterize the sample.

51. A method as recited in claim 50 wherein the modulation frequency of the pump laser beam is varied from 100 KHz to 100 MHz.

52. A method as recited in claim 23 further including the step of varying the size of either of both of the pump and probe laser beam spots on the sample surface and measuring the power of the reflected probe beam at a plurality of pump and probe beam spot sizes and using the measurements to characterize the sample.

53. A method as recited in claim 23 further including the step of measuring the periodic angular deflections of the probe laser beam and using those measurements to evaluate the characteristics of the sample.

54. A method as recited in claim 23 further including the step of measuring the intensity of rays within the probe laser beam as a function of the angle of incidence with respect to the sample surface and using the angle of incidence measurements to evaluate the characteristics of the sample.

55. A method as recited in claim 23 further including the step of measuring the change in polarization state of the reflected probe beam and using the measurements to evaluate the characteristics of the sample.

56. A method as recited in claim 55 wherein the step of measuring the change of polarization state of the reflected probe beam includes generating an output signal that represents an integration of rays within the probe beam having multiple angles of incidence with respect to the sample surface.

* * * * *